(12) United States Patent
Schultz et al.

(10) Patent No.: US 12,228,487 B2
(45) Date of Patent: Feb. 18, 2025

(54) METHOD AND SYSTEMS FOR CHARACTERIZATION OF VISCOUS FLUIDS

(71) Applicant: THE REGENTS OF THE UNIVERSITY OF MICHIGAN, Ann Arbor, MI (US)

(72) Inventors: William W. Schultz, Ann Arbor, MI (US); Subramaniam Balakrishna, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 263 days.

(21) Appl. No.: 17/991,502

(22) Filed: Nov. 21, 2022

(65) Prior Publication Data

US 2023/0160802 A1    May 25, 2023

Related U.S. Application Data

(60) Provisional application No. 63/281,362, filed on Nov. 19, 2021.

(51) Int. Cl.
G01N 11/16    (2006.01)
G01N 9/00     (2006.01)
G01N 33/487   (2006.01)

(52) U.S. Cl.
CPC ......... G01N 11/165 (2013.01); G01N 33/487 (2013.01); *G01N 9/002* (2013.01); *G01N 11/167* (2013.01); *G01N 2203/0094* (2013.01)

(58) Field of Classification Search
CPC ............... G01N 11/165; G01N 33/487; G01N 2203/0094; G01N 9/002; G01N 11/167
See application file for complete search history.

(56) References Cited

U.S. PATENT DOCUMENTS 5,565,620 A  * 10/1996  Bohlin ................... G01N 11/16
                                                        73/61.65
6,711,941 B2 *  3/2004  Braithwaite ............. G01N 3/08
                                                        73/54.01

OTHER PUBLICATIONS

Anna et al., Elasto-capillary thinning and breakup of model elastic liquids, Journal of Rheology, 45(1):115-138 (2001).
Balakrishna et al., Finite differences for higher order derivatives of low resolution data, Mathematics and Computers in Simulation (2021).
Balakrishna et al., Optimal Capillary Breakup Rheometer Procedures for Newtonian Filaments, In APS Division of Fluid Dynamics Meeting Abstracts, pp. G01-003 (Nov. 2019).

(Continued)

*Primary Examiner* — Peter J Macchiarolo
*Assistant Examiner* — John M Royston
(74) *Attorney, Agent, or Firm* — MARSHALL, GERSTEIN & BORUN LLP

(57) ABSTRACT

Methods and systems for characterizing multiple parameters of viscous fluid simultaneously are provided. By imposing an oscillatory deformation profile on a filament formed of the viscous fluid between two plates, a nonlinear fit to the deformation profile captured at different times is analyzed against a filament model dependent upon the plates radius, viscous fluid density, and the oscillation frequency of the imposed deformation profile. The Reynolds number, Weber number, and the aspect ratio of the viscous fluid are thus determined, for identifying the Newtonian fluid.

8 Claims, 6 Drawing Sheets

(56) References Cited

OTHER PUBLICATIONS

Balakrishna et al., Small amplitude oscillatory extensional rheometry for Newtonian filaments, APS Divis. Fluid Dynam., A16.007 (2021).
Balakrishna et al., Small Amplitude Oscillatory Extensional Rheometry for Viscoelastic Filaments, APS Divi. Fluid Dynam., (2022).
Balakrishna, Optimal Capillary Rheometer Methods for Newtonian Fluids, Thesis. U. Michigan, (2021).
Bazilevsky et al., Liquid filament microrheometerand some of its applications, In Third European Rheology Conference and Golden Jubilee Meeting of the British Society of Rheology, 41-43 (1990).
Bejenariu et al., Large amplitude oscillatory extension of soft polymeric networks, Rheologica acta., 49(8):807-814 (2010).
Bhat et al., Formation of beads-on-a-string structures during break-up of viscoelastic filaments, Nat. Phys., 6(8):625-631 (2010).
Brenner et al., Pinching threads, singularities and the No. 0.0304 . . . , Phys. Fluids, 8(11):2827-2836 (1996).
Canny, A computational approach to edge detection, IEEE Trans. Pattern Anal. Mach. Intell., 8(6):679-698 (1986).
Carpenter, The Secretion, Components, and Properties of Saliva, Annual Review of Food Science and Technology, 4(1):267-276 (2013).
Christersson et al., Film-forming properties and viscosities of saliva substitutes and human whole saliva, European Journal of Oral Sciences, 108(5):418-425 (2000).
Desprat et al., Microplates-based rheometer for a single living cell, Rev. Sci. Instrum., 77:055111 (2006).
Eggers et al., Drop formation in a one-dimensional approximation of the Navier-Stokes equation, Journal of Fluid Mechanics, 262:205-221 (1994).
Eggers, Nonlinear dynamics and breakup of free-surface flows, Rev. Mod. Phys., 69(3):865-930 (1997).
Eggers, Universal pinching of 3D axisymmetric free-surface flow, Phys. Rev. Lett., 71(21):3458-3460 (1993).
Haward et al., Extensional rheology of human saliva, Rheologica acta, 50(11-12):869-879 (2011).
Kaplan et al., The functions of saliva, Dysphagia, 8(3):225-229 (1993).
Kolte et al., Capillary thinning of polymeric filaments, Journal of Rheology, 43(3):609-625 (1999).
Liang et al., Rheological characterization of the time and strain dependence for polyisobutylene solutions, Journal of Non-Newtonian Fluid Mechanics, 52(3):387-405 (1994).
Matta et al., Liquid stretching using a falling cylinder, J. Non-Newton. Fluid. Mech., 35(2-3):215-229 (1990).
McCarroll et al., Differential analysis of capillary breakup rheometry for Newtonian liquids, Journal of Fluid Mechanics, 804:116-129 (2016).
McCarroll, One-dimensional Differential Newtonian Analysis for Applications in Saliva Rheology, PhD diss., (2017).
McKinley et al., How to extract the Newtonian viscosity from capillary breakup measurements in a filament rheometer, Journal of Rheology, 44(3):653-670 (2000).
Padday et al., Menisci at a free liquid surface: surface tension from the maximum pull on a rod, J. Chem. Soc. Faraday Trans., 171:1919-1931 (1975).
Papageorgiou, On the breakup of viscous liquid threads, Phys. Fluids, 7(7):1529-1544 (1995).
Paul et al., Oscillatory extensional rheology of microscale fluid filaments, Rheologica Acta, 56(2):113-122 (2017).
Renardy, Some comments on the surface-tension driven break-up (or the lack of it) of viscoelastic jets, J. Non-Newton. Fluid Mech., 51(1):97-107 (1994).
Rodd et al., Capillary break-up rheometry of low-viscosity elastic fluids, Applied Rheology, 15(1):12-27 (2005).
Schultz et al., One-dimensional liquid fibers, J. Rheol., 26(4):331-345 (1982).
Spiegelberg et al., The role of end-effects on measurements of extensional viscosity in filament stretching rheometers, J. Non-Newton. Fluid Mech., 64(2-3):229-267 (1996).
Stokes et al., Viscoelasticity of human whole saliva collected after acid and mechanical stimulation, Biorheology, 44(3):141-160 (2007).
Tirtaatmadja et al., A filament stretching device for measurement of extensional viscosity, J. Rheol., 37(6):1081-1102 (1993).
Wagner, An experimental and theoretical investigation of the rheological properties and degradation of mucin solutions:(or why saliva becomes watery when removed from your mouth), Doctoral dissertation, Massachusetts Institute of Technology (2015).
Zhou et al., Single Polymer Dynamics under Large Amplitude Oscillatory Extension, Phys. Rev. Fluid., 1 (5): 1-17 (2016).

* cited by examiner

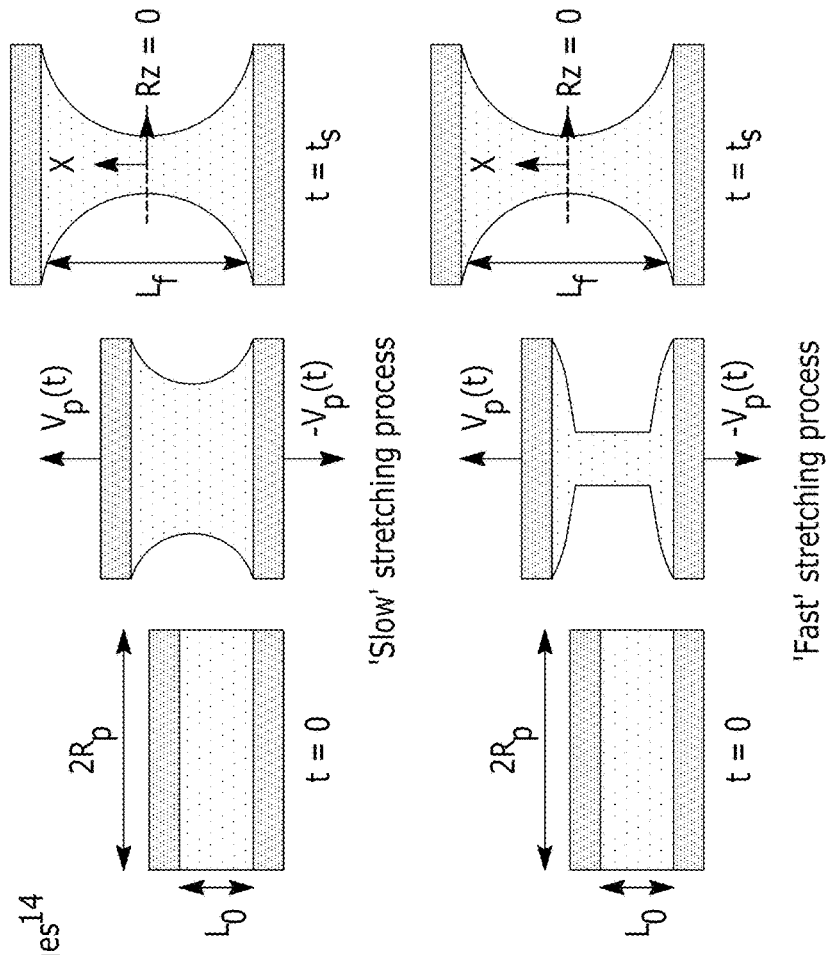

Challenges:
- $R_{zzzz}$ hard to evaluate experimentally from pixelated images[14]
- Traditional CBR evaluate α after stretch
  — Slow stretch leads to nearly static solution
  — Rapid stretch leads to nearly cylindrical filament
  — Optimal stretch speed for viscous filaments[15]
- Traditional Newtonian CBR
  - Allows for characterization of one dynamic property[8]
  - Range limited to $\mu > 70$ mPa-s[16] (70x that of water)
- Low-viscosity filaments
  - Break up before the end of stretch[16]
  - Effects of inertia (Prior Art)
FIG. 2

Inertio-visco-capillary problem

200

- One-dimensional model[17,18], scaled by $R_p$, $\rho$ and $\omega$ $(R^2)_t + (wR^2)_z = 0$, $\rho(w_t + ww_z)R^2 = \frac{-1K_zR^2}{We} + \frac{3(w_zR^2)_z}{Re}$, where $Re = \frac{\rho R_p^2 \omega}{\mu}$ and $We = \frac{\rho R_p^3 \omega^2}{\sigma}$

- BCs: $v_p(t) = \hat{A}e^{it}$, ($\hat{A} << 1$, $\hat{A}$ normalized to 1) $R = 1$ at $z = \pm \Lambda(t)/2$

202

- Linearize 1D eqns. with $R(z,t) = 1 + \hat{R}(z)e^{it}$, $w(z,t) = \hat{w}(z)e^{it}$, $\hat{w}'''' + (1 - 6i We)\frac{\hat{w}''}{Re} - We\hat{w} = 0$

204

- Resulting equations solved for periodic solutions, $\hat{R}(z) = \frac{-i}{2}\sum_{j=1}^{4} c_j m_j e^{m_j z}$, where $c_j = c_j(Re, We, \Lambda_0)$, $m_j = m_j(Re, We, \Lambda_0)$

METHOD AND SYSTEMS FOR CHARACTERIZATION OF VISCOUS FLUIDS

CROSS-REFERENCE TO RELATED APPLICATIONS

This application claims priority to U.S. Provisional Patent Application No. 63/281,362, filed Nov. 19, 2022, the entire disclosure of which is incorporated herein by reference.

STATEMENT OF GOVERNMENT SUPPORT

This invention was made with government support under CBET1604903 awarded by the National Science Foundation. The government has certain rights in the invention.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Identifying and differentiating Newtonian and non-Newtonian fluids has wide ranging applications. An example biological application is identifying properties of saliva. The term "sticky saliva" is a subjective description by health professionals to indicate abnormal salivary mechanics. Sticky saliva is linked to oral health issues, like cavities and xerostomia, and may indicate systemic health conditions, such as multiple sclerosis and HIV (human immunodeficiency virus). Therefore, quantifying saliva's "stickiness" with physics-based metrics (i.e., viscosity, surface tension, elasticity) can be valuable for understanding the relationship between fluid mechanics of saliva and health outcomes.

Advantageously, assessing salivary fluid diagnostics is less intrusive than performing blood diagnostics. However, saliva fluid properties can change considerably during the day depending on eating and drinking schedule, and the properties can change once extracted from the oral cavity. The second challenge is the small sample volumes typically obtained, especially in patients suffering from dysphagia.

Conventionally, for saliva and other polymeric media and flows involving a combination of shear and extension, extensional effects are dominant. Therefore, characterizing such fluids or any low-viscosity elastic fluids, an assessment of extension properties from kinematic behavior is determined.

Capillary breakup rheometry (CBR), for example, is a traditional method to characterize the extensional properties of filament forming fluids. A CBR system includes a sample placed between two parallel plates. These plates are rapidly extended to impose an approximate uniaxial step strain. The resulting filament evolves under the action of viscous, capillary, inertial, elastic, and gravitational forces. Measurements are then made in the vicinity of the filament midpoint (where the radius R is at a local maximum or minimum), usually close to filament breakup (R(t)→0).

CBR, however, neglects inertia and gravity to give an expression for surface tension to viscosity ratio, a (termed ratio hereon). The control volume analysis (gravity and inertia neglected) results in $$\alpha = \frac{\sigma}{6\mu} = \frac{-R_t/R - F/6\mu\pi R^2}{k - 2/R}$$

where $R_z=0$ (see, FIG. 1). Here, subscripts denote partial derivatives with respect to the axial coordinate $-z$ and time $-t$. Notably, the expression contains an axial force F that is hard to measure for low viscosity fluids.

There are other techniques beyond CBR that are also limited in properly measuring and assessing extension properties of fluid. Some have proposed a global analysis to determine F, while others set F=0 since the filament is attached to quasi-static reservoirs. Curvature, K is approximated as 1/R at lowest order, and the resulting expression severely underpredicts the ratio $\alpha$ for many Newtonian fluids. Others argue that F approaches the perimeter term ($2\pi\sigma R$) as the filament approaches breakup, resulting in an expression for ratio $\alpha$ that depends on filament breakup.

A promising technique is that of McCarroll, L. L., Solomon, M. J. and Schultz, W. W., 2016, Differential analysis of capillary breakup rheometry for Newtonian liquids. *Journal of Fluid Mechanics*, 804, pp. 116-129. McCarroll et al. make only one assumption (rectilinear flow near the midpoint) and retain full curvature. The resulting expression is:

$$\alpha = \frac{3R_t R_{zz} - RR_{zzt}}{k_{zz}R^2} = \frac{1}{3\nu k_{zz}R^2}\left(3R_t^2 - RR_{tt}\right)$$

where $R_z=0$

To evaluate the ratio $\alpha$, accurate measurements and spatial and temporal derivatives of these measurements of the free surface radius are required, where these measurements are made with a digital camera. Note, however, that the second and fourth spatial derivatives of free surface radius are present in $\kappa_{zz}$.

The challenges in McCarroll et al. (see, e.g., FIG. 2) are twofold: (i) the fourth derivative of free surface radius is hard to evaluate from pixelated images; and (ii) rapid stretch results in a cylindrical filament with hard to measure gradients, while slow stretch results in a quasi-static solution with no noticeable viscous effects. Optimal stretch histories are therefore necessary for more accurate measurements. Traditional Newtonian CBR usually provides one property (viscosity), while the other (surface tension) is determined through other methods. Further, there is a limited range of viscosities that can be evaluated from these methods, primarily due to the finite time it takes to impose a step strain.

SUMMARY OF THE INVENTION

The present techniques provide for systems and methods for characterizing Newtonian fluids to overcome the deficiencies of conventional techniques.

In accordance with an example, a method for characterizing a viscous fluid sample, includes: with the viscous fluid sample mounted between parallel plates, each having a circle shape and having a radius, $R_p$, and spaced apart from one another a spacing distance, L, imposing an oscillatory movement on at least one of the parallel plates to create an extension and contraction on the spacing distance, L, thereby imposing an oscillation on a resulting filament of the viscous fluid sample therebetween; obtaining images of a profile of the filament of the viscous fluid sample captured at different points during the oscillation cycle and identifying filament profiles in the images; and for each obtained image, performing a nonlinear regression curve fit on the filament profiles and comparing the nonlinear regression curve fits to a periodic solution to a one-dimensional (1D) model for a radius of the resulting filament, the 1D model being scaled by the radius, $R_p$, a density of the viscous fluid sample, and an oscillation frequency, ω, of the oscillatory movement, where the periodic solution is formed of coefficients that are each a function of a Reynolds number, a Weber number, and an initial aspect ratio of the viscous fluid sample that is a ratio of an initial spacing distance, $L_0$, to the radius, $R_p$; and determining from the comparison surface tension, viscosity to density, or relaxation, of the viscous fluid sample.

In an aspect, imposing the extension and contraction on the spacing distance between the parallel plates to impose the oscillation on the resulting filament is achieved by applying an oscillating signal to move at least one of the parallel plates.

In an aspect, imposing the extension and contraction on the spacing distance between the parallel plates to impose the oscillation on the resulting filament is achieved by applying an oscillating signal to move each of the parallel plates.

In an aspect, oscillation comprises a sinusoidal oscillation on the spacing distance, L.

In an aspect, The method of claim 1, wherein the aspect ratio is ≤1.

In an aspect, the periodic solution is:

$$\hat{R}(z) = \frac{-i}{2}\sum_{j=1}^{4} c_j m_j e^{m_j z}.$$

where the coefficients of the period solution are $c_j=c_j(Re, We, \Lambda_0)$ and where R(z) is the radius as a function of z value from a center plane of the spacing distance, L.

In an aspect, the nonlinear regression curve fit is a Gauss Newton linear regression curve fit.

In an aspect, the nonlinear regression curve fit is a least squares curve fit.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIG. 2 is a listing of limitations and challenges in performing capillary breakup rheometry (CBR), according to the prior art.

FIGS. 4-6 illustrate a process for characterizing a viscous fluid sample, in accordance with an example.

DETAILED DESCRIPTION

The present techniques provide for systems and methods for characterizing viscous fluids to overcome the deficiencies of conventional techniques.

The techniques herein provide unique methods by which stretching properties and filament properties of a viscous fluid sample can be determined. Indeed, the techniques herein may be used to differentiate between Newtonian and non-Newtonian materials that do not exhibit linear viscosity under stress.

The present techniques are able to overcome the foregoing discussed deficiencies in the prior art. The present techniques are able to consider stretch histories during viscous fluid analysis, thus avoiding the "filament break-up" that plagues certainty CBR techniques. Multiple parameters can be characterized simultaneously, with the present techniques. That includes use of inertia in filament dynamics. And the analyses herein may be based on a small set of properties: a fluid density, oscillation frequency, and a radius of the plates between which a sample is placed. By imposing an oscillatory deformation profile on the filament and comparing against images of the profile, the present techniques are able to characterize viscous fluid properties.

Figure 1:
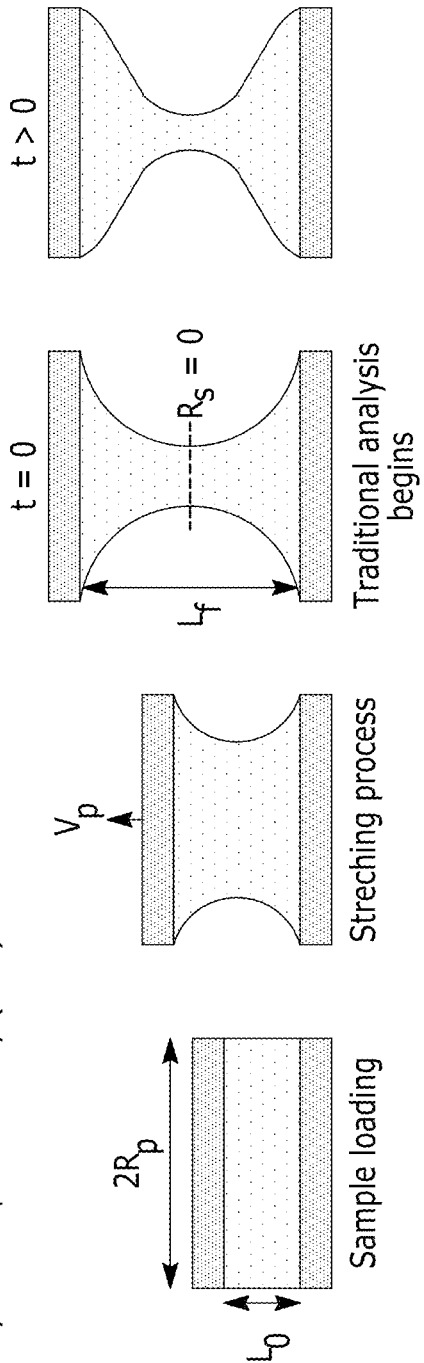
FIG. 1 is a listing of example expressions for performing capillary breakup rheometry (CBR), according to the prior art.
Figure 3:
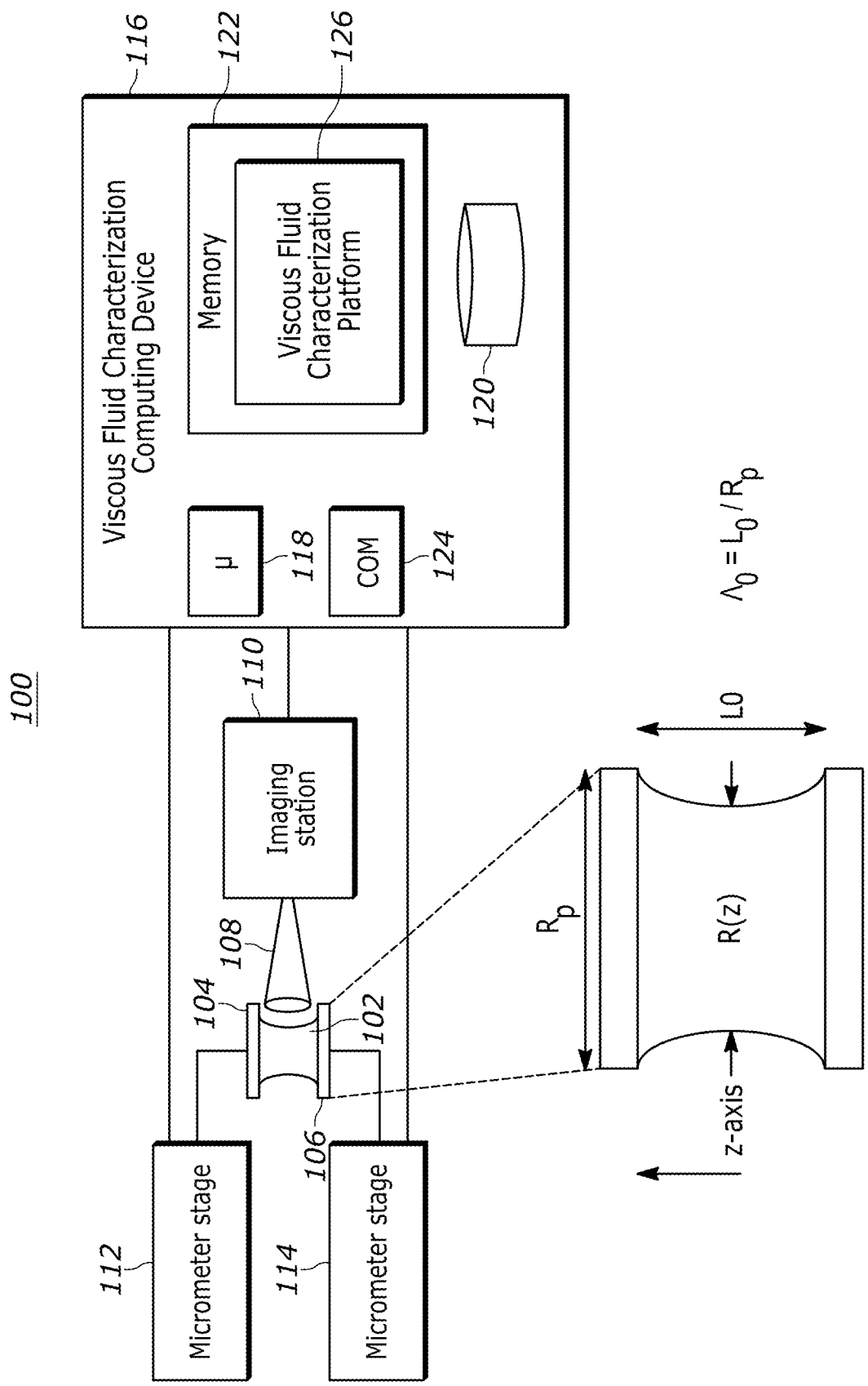
FIG. 3 illustrates a 1D model of a filament, scaled by the radius of the plate $R_p$, the density, ρ and an external frequency ω, in accordance with an example.

FIG. 3 illustrates a system 100 for analyzing a sample having viscous fluid, as may be used to implement the processes and methods herein, including to characterize the viscous fluid. The system 100 includes a sample 102, which may be any viscous fluid or material containing or coinciding with viscous fluid to be analyzed in accordance with techniques herein. For example, the system 100 may be used for applications such as to perform viscosity measurements of polymers, assess viscous materials used for high concentration mineral suspension systems in the mining and minerals industry, or analysis of complex polymeric viscoelastic materials-based adhesives and sealants. Other examples include analysis of artificial fibers, coatings, and saliva.

In the illustrated example, the sample 102 is maintained between two parallel, circular shaped plates 104 and 106, each of radius, $R_p$, and separated by an initial distance, $L_0$, in the illustrated example, that position the sample 102 within an imaging field of view (FOV) 108 of an imaging station 110, having a high-resolution imager, such as a bright light charged-coupled device (CCD) imager or other imaging device. To affect analysis of the sample 102, movement of the plates 104 and 106 are controlled by micrometer adjustment stages 112 and 114, respectively. For example, these adjustment stages 112/114 may be configured to move the plates 104/106 within a XYZ three-dimensional (3D) space. In particular, the plates 104/106 may be translated and/or rotated with the XYZ space. Further, the plates 104/106 may be controlled to impose small oscillations on the sample 102 along any generally parallel orientation of the plates within the XYZ space.

The environment 100 includes a computing device 116 configured to perform viscous fluid characterization in accordance with various processes and methods herein. The computing device 116 includes a includes one or more processing units 118, a local data storage 120, a computer-readable memory 122, and communication interface 124, which may include a network interface and/or Input/Output (I/O) interfaces connecting the computing device 116 to the imaging station 110, the micrometer stages 112/114, a display (not shown), user input device (not shown), a communication network (not shown), or other devices or systems.

The computing device 116 may be implemented on a single computer processing device or multiple computer processing devices. The computing device 116 may be implemented on a network accessible computer processing device, such as a server, or implemented across distributed devices connected to one another through a communication link. In other examples, functionality of the computing device 116 may be distributed across any number of devices, including the portable personal computer, smart phone, electronic document, tablet, and desktop personal computer devices shown. In other examples, the functionality of the computing device 116 may be cloud based, such as, for example one or more connected cloud CPU(s) customized to perform machine learning processes and computational techniques herein.

The communication interface 124 may include a network interface connected to a network (not shown) that may be a public network such as the Internet, private network such as research institution's or corporation's private network, or any combination thereof. Networks can include, local area network (LAN), wide area network (WAN), cellular, satellite, or other network infrastructure, whether wireless or wired. The network can utilize communications protocols, including packet-based and/or datagram-based protocols such as internet protocol (IP), transmission control protocol (TCP), user datagram protocol (UDP), or other types of protocols. Moreover, such a network may include a number of devices that facilitate network communications and/or form a hardware basis for the networks, such as switches, routers, gateways, access points (such as a wireless access point as shown), firewalls, base stations, repeaters, backbone devices, etc.

The memory 122 may be a computer-readable media and may include executable computer-readable code stored thereon for programming a computer (e.g., comprising a processor(s) and GPU(s)) to the techniques herein. Examples of such computer-readable storage media include a hard disk, a CD-ROM, digital versatile disks (DVDs), an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. More generally, the processing units 122 of the computing device 116 may represent one or more CPU-type processing units, one or more GPU-type processing units, one or more a field-programmable gate arrays (FPGA), another class of digital signal processor (DSP), or other hardware logic components that can be driven by a CPU.

In the illustrated example, in addition to storing an operating system (not shown), the memory 122 stores a viscous characterization platform 126, configured to execute various processes described and illustrated herein. In an example, the viscous characterization platform 126 is configured to characterize a viscous fluid sample. For example, the platform 126 may be configured with a one-dimensional (1D) model of a filament of a viscous fluid sample between the plates 104/106 or with a periodic solution of differential equations determined from that 1D model, that periodic solution being scaled by the radius, $R_p$, a density of the viscous fluid sample, and an oscillation frequency, $\omega$, of an oscillatory movement of the plates 104 and 106 relative to one another. The periodic solution may be characterized by coefficients that are each a function of a Reynolds number, a Weber number, and an initial aspect ratio, $\Lambda_0$, of the viscous fluid sample that is a ratio of an initial spacing distance, $L_0$, to the radius, $R_p$.

Figure 5:
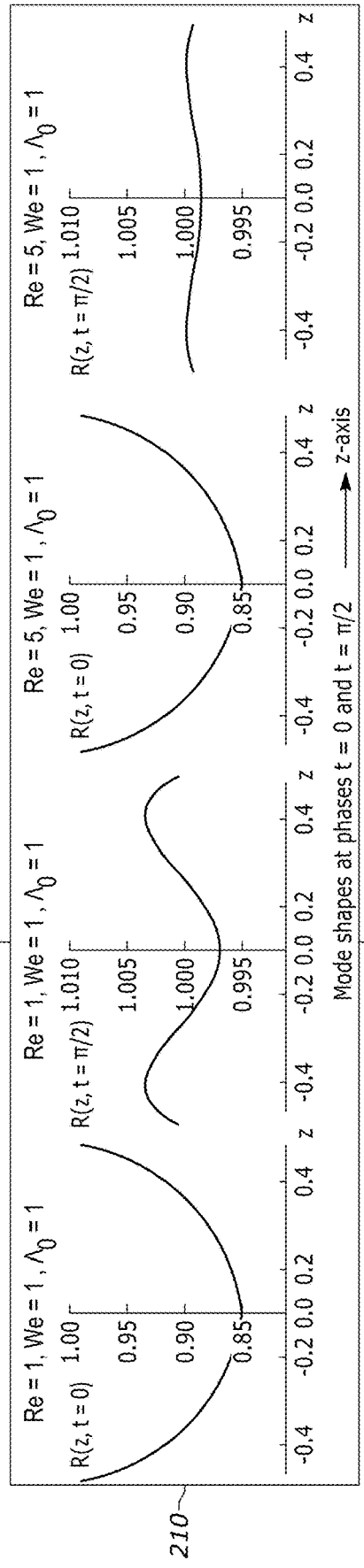
Figure 6:
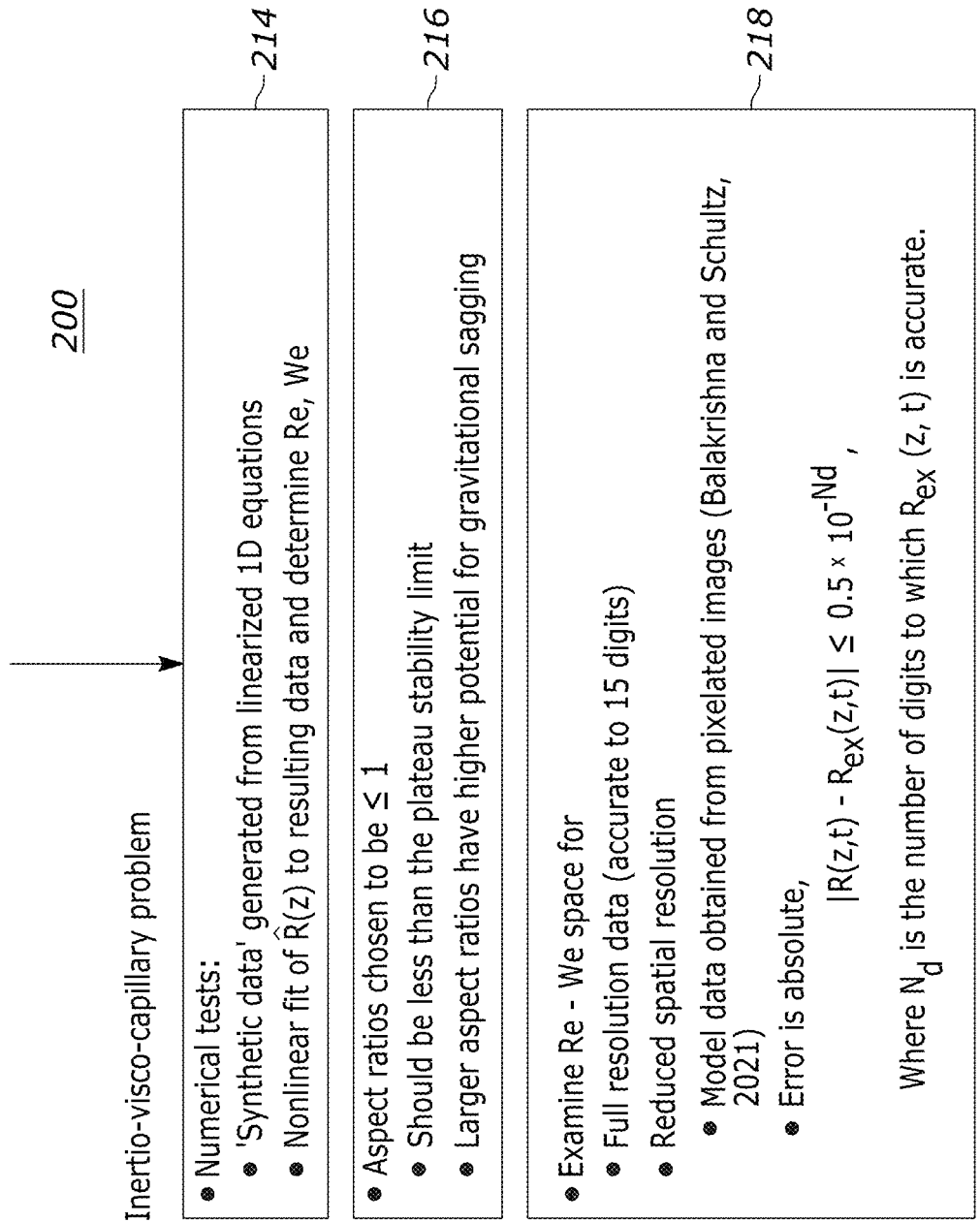

In various examples, the viscous characterization platform 126 is configured to perform viscous characterization using a method 200 as shown in FIGS. 4-6. The method 200 provides development of a 1D model of a filament profile and a periodic solution thereof that is solved using image data and curve fitting to filament profiles identified characteristics of a viscous fluid sample.

FIG. 4 illustrates that the process 200 is initiated, at a block 202, by forming a one-dimensional (1D) model of a filament, such as a sample of viscous fluid. At the block 202, the 1D model is scaled by a radius of the plate or plates, $R_p$, the density, $\rho$ and an external frequency $\omega$. We note that in some examples, including that illustrated, the density of the fluid is treated as known, e.g. this property is typically measurable or known. For saliva, for example, the density of water can serve as an excellent approximation. In implementing the viscous characterization platform 126, the process 200 may be configured to consider deformation profiles that avoid breakup of the filament, namely small amplitude oscillatory motion. A block 204 linearizes the 1D equations and eliminating one variable generates in a periodic solution in the complex form $R(z, t) = 1 + \hat{R}(z)e^{it}$ for the free surface, resulting in equations solved for periodic solutions at block 206. Note that the solution is a nonlinear function of Reynolds (Re), Weber number (We) and aspect ratio ($\Lambda_0$). In an example, the block 206 stores a periodic solution to the 1D model in the form of the expression:

$$\hat{R}(z) = \frac{-i}{2} \sum_{j=1}^{4} c_1 m_1 e^{m_j z}.$$

where $c_j = c_j(Re, We, \Lambda_0)$, $m_j = m_j(Re, We, \Lambda_0)$.

The coefficients obtained in the periodic solution, $c_j$ and $m_j$, are functions of Reynolds number and Weber number, as well as the aspect ratio of $L_0/R_p$, as shown in FIG. 3. Therefore, if $\hat{R}(z)$ is reconstructed and fitted with an analytical solution, for example, taken from obtained images, multiple parameters can be characterized, from which various viscous fluid properties are determined. Further, no spatial or temporal derivatives of the data are required to evaluate these parameters. Oscillation of the filament has an initial transient but quickly becomes periodic.

Continuing in in FIG. 5, in order to reconstruct $\hat{R}$ (a complex function), digital images of the free surface of the filament (e.g., sample) at $t=0$ and $t=\pi/2$, were taken at a block 208, from which the real and imaginary parts of $\hat{R}$, respectively. The block 208 provides an oscillation signal, for example, a voltage, $v_p(t)$ having an oscillation frequency, $\omega$, to move one or both of the plates 104 and 106 along the z-axis. This resulting oscillatory movement may extend and contract the spacing distance, L, between the plates 104 and 106 making that spacing distance a function of time, t. The applied voltage may be a sinusoidal voltage $v_p(t) = A \omega \sin(\omega t)$, for example.

The block 208 obtains images of the filament (as shown in the filament profile of the sample 102 in FIG. 3) formed of the viscous fluid sample at different points in time, for example, at $t=0$ and $t=\pi/2$. The block 208 identifies a curved filament surface or two curved filament surfaces as the filament profile and performs a nonlinear regression fit to reconstruct $\hat{R}$ from the filament profiles in the obtained images. From the nonlinear regression fit to $\hat{R}$, the nonlinear regression fit is compared to the periodic solution stored at block 206 and the coefficients $c_j$ and $m_j$ are determined and from those Re and We values are determined, density to viscosity ratio and density to surface tension ratio, respectively. Example nonlinear regression fits for different points in time and resulting from different Re and We values, with an aspect ratio $\Lambda_0 = 1$, are shown in block 210. The block 208 thus can determine various viscous fluid characteristics, such as, surface tension to viscosity ratio, surface tension, a surface tension to density ratio, a viscosity to density ratio, and/or viscosity. Further, the block may determine relaxation times in viscous fluids.

As indicated in block 206 of FIG. 4, the function $\hat{R}$ depends nonlinearly on Re and We. We therefore used a nonlinear regression fitting procedure, in various examples herein. Our numerical experiments (see, e.g., the configuration assumptions in block 212 of FIG. 5) indicate that the choice of four complex parameters is easier than their corresponding either real or imaginary parts. In the illustrated example, the blocks 208/210 may be configured to apply the Gauss-Newton method for nonlinear regression, with an inexact line search to accelerate convergence. Other least squares procedures such as gradient descent and LM (Levenberg-Marquardt) may be used, but are far slower to converge (~100 iterations, in contrast with ~10 iterations for Gauss Newton), in our tested examples.

To examine the operational space of the process 200, we performed numerical tests (see, FIG. 6). At a block 214, synthetic data was generated from the linearized 1D equations—$\hat{R}$ was then fit to this data to determine the desired properties in nondimensional form. In the process 200, at a block 216, the aspect ratio of the filament profile was determined from previous studies of extensional rheometry. Notably, bridges with large aspect ratios are (a) closer to the Plateau stability limit and (b) have a higher potential to sag under the influence of gravity. Therefore, we examined bridges with smaller aspect ratios. Further, because post-processed images from a digital imaging station are used to reconstruct $\hat{R}$, at a block 218, the process 200 examined the Re-We parameter space for full (15 digit) and reduced spatial resolution, to better understand the sensitivity of our method to spatial errors from pixelated digital images. In an example, we show a model of 'pixelation' that rounds the 'synthetic data' to the required resolution, typically 4 to 6 digits for carefully measured data.

In examining the aspect ratio of the Re-We parameter space, the block 218 was configured to consider a grid spacing of 100 points for regression, with the 1000-point case providing comparable results, and an aspect ratio of 1. The results of the curve fitting procedure were then monitored from which the block 218 determined the errors in the converged values of Re and We. We also examined, at the block 218, the choice of initial iterate on the converged solution—an initial iterate that is two orders of magnitude from the exact solution in both Re and We served as an excellent starting point to obtain an accurate converged result. Our results indicated that optimal measurements of Re and We are obtained for Re~1 and We~1, with the error being $O(10^{-8})$ for full precision data.

We also examined the Re-We parameter space for reduced resolution data. The previous analyses of CBR by McCarroll et al., for example, indicated that sub-pixel resolution can be obtained through post-processing by grey scales and smoothing of images. We therefore examined the Re-We parameter space for four- and five-digit accuracies. And in an example, our computations indicated that 5-digit accuracy in $\hat{R}$ would obtain an error less than 1% in Re and We.

We note that boundary layers exist at the plates of the sample, with the physics being markedly different when compared to the 1D model. We therefore examined the effect of window size (away from the plates) where experimental data is compared to the 1D model. We examined the effect of a window that covers 20%-50% of the domain. Our results indicated that for five digit-accuracy, a domain size of 40% is appropriate.

As noted, the block 214 may implement a nonlinear regression to perform a curve fit on the image of the filament to $\hat{R}$. Examples curve fits include a Gauss-Newton method curve fit, a gradient descent method, a Levenberg-Marquardt (LM) method, a linearized Maxwell model, or a linearized Jeffrey model.

As described, the present application provides for systems and methods of modified capillary rheometry, using an oscillatory stretch history and corresponding analysis. The methods herein allow for determination of multiple physical parameters in extension when density is treated as a known parameter and require no spatial/temporal derivatives. Further, using a small amplitude condition implies that the location of the free surface is very compact, allowing for further improvement in resolution in the radial direction. Coupled with control over sample volumes and ω, Re and We over a dynamic range can be examined with the methods herein. In particular, low-viscosity fluids like water and saliva can be characterized in contrast to traditional CBR.

Further still, the methods herein can be extended to determine a relaxation time and retardation time for linear viscoelastic materials. For example, the blocks 202-206 can be implemented to determine a 1D model and periodic solution R(z) for determining relaxation time as a viscous fluid characteristic. In some examples, such determinations are made using a linearized Maxwell model or linearized Jeffrey model may be used, as follows.

Example Linearized Maxwell Model

We now consider the evaluation of a single relaxation time for a linear viscoelastic fluid, obeying the Maxwell model. The 1-D bulk continuity and axial momentum equations, scaled by $R_p$ (radius of the plate), ρ and ω (external timescale) are $$(R^2)_t + (wR^2)_z = 0, \; (w_t + ww_z)R^2 = -\frac{1}{We}\kappa_z R^2 + \left[(\tau^{zz} - \tau^{rr})R^2\right]_z,$$

$$\kappa = \frac{1}{R(1+R_z^2)} - \frac{R_{zz}}{(1+R_z^2)^{3/2}}, \; (\tau^{zz} - \tau^{rr}) + De(\tau^{zz} - \tau^{rr})_t = \frac{3}{\text{Re}}w_z,$$

where $$We = \frac{\rho R_0^3 \omega^2}{\sigma}, \; \text{Re} = \frac{\rho R_0^2 \omega}{\mu}, \; Ca = \frac{\mu R_0 \omega}{\sigma} \; De = \lambda\omega$$

where λ is the relaxation time and μ is the viscosity of the polymer. Please note that We=Re·Ca, where. Let Λ(t) is harmonic, that is $$\Lambda(t) = \Lambda_0 + \hat{A}e^{it},$$

where $\hat{A}$ is complex. The boundary conditions are $$R(\pm\Lambda(t),t) = 1, w(\pm\Lambda(t),t) = \hat{A}ie^{it}$$

Let $(\tau^{p,zz} - \tau^{p,rr}) = \tau$. The governing equations are linearized by letting $R(z, t) = 1 + \hat{R}(z)e^{it}$, $w(z, t) = \hat{w}(z)e^{it}$, and $\tau(z, t) = \hat{\tau}(z)e^{it}$ to give $$2i\hat{R} + \hat{w}' = 0,$$

$$i\hat{w} = \frac{1}{We}(\hat{R}' + \hat{R}''') + \hat{\tau}',$$

$$(1 + iDe)\hat{\tau} = \frac{3}{\text{Re}}\hat{w}',$$

The BCs are linearized (for z=Λ) as follows $$R(\Lambda_0 + \hat{A}e^{it}, t) = R(\Lambda_0, t) + \hat{A}e^{it}\frac{\partial R}{\partial z}|_{\Lambda_0} + \ldots = 1,$$

which, at lowest order gives
Similarly, for $\hat{w}$, we have $$R(\Lambda_0, t) = 1 + \hat{R}(\Lambda_0)e^{it} = 1 \Rightarrow \hat{R}(\Lambda_0) = 0.$$

$$w(\Lambda_0 + \hat{A}e^{it}, t) = w(\Lambda_0, t) + \hat{A}e^{it}\frac{\partial w}{\partial z}|_{\Lambda_0} + \ldots = \hat{A}ie^{it},$$

which, at lowest order gives
$w(\Lambda_0,t)=\hat{w}(\Lambda_0)e^{it}=\hat{A}ie^{it} \Rightarrow \hat{w}(\Lambda_0)=\hat{A}i$ As in the linear stability analysis, imposing boundary conditions on $\hat{w}$ are far easier. Hence, we solve for $\hat{w}$. The governing equation for $\hat{w}$ is $$\hat{w}'''' + \left(1 - \frac{6i\,Ca}{1+i\,De}\right)\hat{w}'' - 2\text{Re}\cdot Ca\,\hat{w} = 0,$$

whose roots are denoted by $m_i$, i=1, 2, 3, 4. In general, the $m_i$ are distinct. The solutions are then given by $$\hat{w}(z) = \sum_{j=1}^{4} c_j e^{m_j z}.$$

From the boundary conditions, $\hat{w}(\pm\Lambda_0)=0$ and $\hat{w}'(\pm\Lambda_0)=\pm Ai$, we have $$M(\text{Re}, Ca, De, \Lambda)c = \begin{pmatrix} e^{m_1\Lambda} & e^{m_2\Lambda} & e^{m_3\Lambda} & e^{m_4\Lambda} \\ e^{-m_1\Lambda} & e^{-m_2\Lambda} & e^{-m_3\Lambda} & e^{-m_4\Lambda} \\ m_1 e^{m_1\Lambda} & m_2 e^{m_2\Lambda} & m_3 e^{m_3\Lambda} & m_4 e^{m_4\Lambda} \\ -m_1 e^{-m_1\Lambda} & -m_2 e^{-m_2\Lambda} & -m_3 e^{-m_3\Lambda} & -m_4 e^{-m_4\Lambda} \end{pmatrix} c = \begin{pmatrix} Ai \\ -Ai \\ 0 \\ 0 \end{pmatrix} \quad (118)$$

c is then determined analytically from Wolfram Mathematica. The resulting solution yields $\hat{R}(z)$, $$\hat{R}(z) = \frac{-1}{2i}\sum_{j=1}^{4} c_j m_j e^{m_j z}. \quad (119)$$

Example Linearized Jeffrey Model

We now consider the evaluation of a single relaxation time for a linear viscoelastic fluid, obeying the Maxwell model. The 1-D bulk continuity, axial momentum and continuity equations, scaled by $R_o$ (radius of the plate), $\rho$ and $\omega$ (external timescale) are $$(R^2)_t + (wR^2)_z = 0,\; (w_t + ww_z)R^2 = -\frac{1}{We}\kappa_z R^2 + [(\tau^{pzz}-\tau^{p,rr})R^2]_z,$$

$$\kappa = \frac{1}{R(1+R_z^2)} - \frac{R_{zz}}{(1+R_z^2)^{3/2}},$$

$$(\tau^{p,zz}-\tau^{p,rr}) + De_1(\tau^{p,zz}-\tau^{p,rr})_t = \frac{3}{\text{Re}}(w_z + De_2 w_t),$$

where $$We = \frac{\rho R_0^3 \omega^2}{\sigma},\; \text{Re} = \frac{\rho R_0^2 \omega}{\mu},\; De_1 = \lambda_1 \omega,\; \text{and}\; De_2 = \frac{\lambda_2}{\lambda_1}De_1 = kDe_1,$$

where $\lambda_1$ is the relaxation time, $\lambda_2$ is the retardation time and $\mu$ is the viscosity of the polymer. Please note that We=Re Ca, where Ca=$\mu R_0 w/\sigma$. Let $\Lambda(t)$ is harmonic, that is $$\Lambda(t)=\Lambda_0+\hat{A}e^{it},$$

where $\hat{A}$ is complex. The boundary conditions are $$R(\pm\Lambda(t),t)=1, w(\pm\Lambda(t),t)=\hat{A}ie^{it}$$

Let $(\tau^{p,zz}-\tau^{p,rr})=\tau$. The governing equations are linearized by letting $R(z, t)=1+\hat{R}(z)e^{it}$, $w(z, t)=\hat{w}(z)e^{it}$, and $\tau(z, t)=\hat{\tau}(z)e^{it}$ to give $$2i\hat{R} + \hat{w}' = 0,$$

$$i\hat{w} = \frac{1}{We}(\hat{R}' + \hat{R}''') + \hat{\tau}',$$

$$(1+i\,De_1)\hat{\tau} = \frac{3}{\text{Re}}\hat{w}'(1+ik\,De_1),$$

The BC's are linearized (for z=Λ) as follows $$R(\Lambda_0 + \hat{A}e^{it}, t) = R(\Lambda_0, t) + \hat{A}e^{it}\frac{\partial R}{\partial z}|_{\Lambda_0} + \ldots = 1,$$

which, at lowest order gives $R(\Lambda_0,t)=1+\hat{R}(\Lambda_0)e^{it}=1 \Rightarrow (\Lambda_0)=0.$ Similarly, for $\hat{w}$, we have $$w(\Lambda_0 + \hat{A}e^{it}, t) = w(\Lambda_0, t) + \hat{A}e^{it}\frac{\partial w}{\partial z}|_{\Lambda_0} + \ldots = \hat{A}e^{it},$$

which, at lowest order gives $w(\Lambda_0,t)=\hat{w}(\Lambda_0)e^{it}=\hat{A}ie^{it} \Rightarrow \hat{w}(\Lambda_0)=\hat{A}i$ As in the linear stability analysis, imposing boundary conditions on $\hat{w}$ are far easier. Hence, we solve for $\hat{w}$. The governing equation for $\hat{w}$ is $$\hat{w}'''' + \left[1 - 6i\,Ca\left(\frac{1+ik\,De_1}{1+i\,De_1}\right)\right]\hat{w}'' - 2\text{Re}\cdot Ca\,\hat{w} = 0,$$

whose roots are denoted by $m_i$, i=1, 2, 3, 4. In general, the $m_i$ are distinct. The solutions are then given by $$\hat{w}(z) = \sum_{j=1}^{4} c_j e^{m_j z}.$$

From the boundary conditions, $\hat{w}(\pm\Lambda_0)=0$ and $\hat{w}'(\pm\Lambda_0)=\pm Ai$, we have $$M(Re, Ca, De_1, k, \Lambda)c = \begin{pmatrix} e^{m_1\Lambda} & e^{m_2\Lambda} & e^{m_3\Lambda} & e^{m_4\Lambda} \\ e^{-m_1\Lambda} & e^{-m_2\Lambda} & e^{-m_3\Lambda} & e^{-m_4\Lambda} \\ m_1e^{m_1\Lambda} & m_2e^{m_2\Lambda} & m_3e^{m_3\Lambda} & m_4e^{m_4\Lambda} \\ m_1e^{-m_1\Lambda} & m_2e^{-m_2\Lambda} & m_3e^{-m_3\Lambda} & m_4e^{-m_4\Lambda} \end{pmatrix} c = \begin{pmatrix} Ai \\ -Ai \\ 0 \\ 0 \end{pmatrix} \quad (124)$$

c is then determined analytically from Wolfram Mathematica. The resulting solution yields $\hat{R}(z)$, $$\hat{R}(z) = \frac{-1}{2i}\sum_{j=1}^{4} c_j m_j e^{m_j z}.$$

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some operations of the method may be performed by one or more processors or processor-implemented hardware modules. The performance of certain operations may be distributed among the one or more processors, but deployed across a number of machines. In some example embodiments, the processor or processors may be in a single location (e.g., within a home environment, an office environment or as a server farm), while in other embodiments the processors may be distributed across several locations.

The performance of certain of the operations may be distributed among the one or more processors, not only residing within a single machine, but deployed across several machines. In some example embodiments, the one or more processors or processor-implemented modules may be in a single geographic location (e.g., within a home environment, an office environment, or a server farm). In other example embodiments, the one or more processors or processor-implemented modules may be distributed across several geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

What is claimed is:

1. A method for characterizing a viscous fluid sample, the method comprising:
    with the viscous fluid sample mounted between parallel plates, each having a circle shape and having a radius, $R_p$, and spaced apart from one another a spacing distance, L, imposing an oscillatory movement on at least one of the parallel plates to create an extension and contraction on the spacing distance, L, thereby imposing an oscillation on a resulting filament of the viscous fluid sample therebetween;
    obtaining images of a profile of the filament of the viscous fluid sample captured at different points during the oscillation cycle and identifying filament profiles in the images; and
    for each obtained image, performing a nonlinear regression curve fit on the filament profiles and comparing the nonlinear regression curve fits to a periodic solution to a one-dimensional (1D) model for a radius of the resulting filament, the 1D model being scaled by the radius, $R_p$, a density of the viscous fluid sample, and an oscillation frequency, $\omega$, of the oscillatory movement, where the periodic solution is formed of coefficients that are each a function of a Reynolds number, a Weber number, and an initial aspect ratio of the viscous fluid sample that is a ratio of an initial spacing distance, $L_0$, to the radius, $R_p$; and
    determining from the comparison surface tension, viscosity to density, or relaxation, of the viscous fluid sample.

2. The method of claim 1, wherein imposing the extension and contraction on the spacing distance between the parallel plates to impose the oscillation on the resulting filament is achieved by applying an oscillating signal to move at least one of the parallel plates.

3. The method of claim 1, wherein imposing the extension and contraction on the spacing distance between the parallel plates to impose the oscillation on the resulting filament is achieved by applying an oscillating signal to move each of the parallel plates.

4. The method of claim 1, wherein the oscillation comprises a sinusoidal oscillation on the spacing distance, L.

5. The method of claim 1, wherein the aspect ratio is ≤1.

6. The method of claim 1, wherein the periodic solution is:

$$\hat{R}(z) = \frac{-i}{2}\sum_{j=1}^{4} c_j m_j e^{m_j z}$$

where the coefficients of the period solution are $c_j=c_j(Re, We, \Lambda_0)$, $m_j=m_j(Re, We, \Lambda_0)$ and where R(z) is the radius as a function of z value from a center plane of the spacing distance, L.

7. The method of claim 1, wherein the nonlinear regression curve fit is a Gauss Newton linear regression curve fit.

8. The method of claim 1, wherein the nonlinear regression curve fit is a least squares curve fit.

* * * * *

UNITED STATES PATENT AND TRADEMARK OFFICE
CERTIFICATE OF CORRECTION

PATENT NO. : 12,228,487 B2
APPLICATION NO. : 17/991502
DATED : February 18, 2025
INVENTOR(S) : William W. Schultz et al.

Page 1 of 1

It is certified that error appears in the above-identified patent and that said Letters Patent is hereby corrected as shown below:

In the Claims

At Column 12, Line 46, "images; and" should be -- images; --.

Signed and Sealed this
First Day of July, 2025

Coke Morgan Stewart
*Acting Director of the United States Patent and Trademark Office*